(12) United States Patent
Lee et al.

(10) Patent No.: US 11,534,584 B2
(45) Date of Patent: Dec. 27, 2022

(54) MICROACTUATOR SYSTEMS, DRAINAGE DEVICES EQUIPPED THEREWITH, AND METHODS OF USE

(71) Applicant: Purdue Research Foundation, West Lafayette, IN (US)

(72) Inventors: Hyowon Lee, West Lafayette, IN (US); Qi Yang, Philadelphia, PA (US)

(73) Assignee: Purdue Research Foundation, West Lafayette, IN (US)

( * ) Notice: Subject to any disclaimer, the term of this patent is extended or adjusted under 35 U.S.C. 154(b) by 339 days.

(21) Appl. No.: 16/689,203

(22) Filed: Nov. 20, 2019

(65) Prior Publication Data

US 2020/0155820 A1 May 21, 2020

Related U.S. Application Data

(60) Provisional application No. 62/769,783, filed on Nov. 20, 2018.

(51) Int. Cl.
*A61M 27/00* (2006.01)
*A61M 25/00* (2006.01)

(52) U.S. Cl.
CPC ... *A61M 27/006* (2013.01); *A61M 2025/0019* (2013.01); *A61M 2205/0294* (2013.01); *A61M 2205/332* (2013.01); *A61M 2205/3334* (2013.01); *A61M 2210/125* (2013.01)

(58) Field of Classification Search
CPC ........ A61M 27/006; A61M 2025/0019; A61M 2205/0294; A61M 2205/332; A61M 2205/3334; A61M 2210/125; A61M 25/0017
See application file for complete search history.

(56) References Cited

U.S. PATENT DOCUMENTS

| | | | | |
|---|---|---|---|---|
| 2006/0241545 A1* | 10/2006 | Madsen | ............... | A61M 27/006 604/9 |
| 2007/0209437 A1* | 9/2007 | Xue | ........................ | G01L 9/007 73/514.31 |
| 2008/0281250 A1* | 11/2008 | Bergsneider | ........ | A61M 25/007 604/9 |

(Continued)

OTHER PUBLICATIONS

Lee, Hyowon et al., "Evaluation of Magnetic Resonance Imaging Issues for Implantable Microfabricated Magnetic Actuators," Biomed Microdevices (2014) 16 pp. 53-161.

(Continued)

*Primary Examiner* — Tatyana Zalukaeva
*Assistant Examiner* — Hans Kaliher
(74) *Attorney, Agent, or Firm* — Hartman Global IP Law; Gary M. Hartman; Domenica N. S. Hartman

(57) ABSTRACT

Drainage devices and microactuator systems adapted to be incorporated into drainage devices to provide a self-clearing capability for reducing obstructions in the drainage devices and/or a self-monitoring capability to confirm the overall operating condition of the drainage devices and their microactuators. Such a microactuator system includes a microactuator having a base, a cantilever comprising a flexure extending from the base and a plate structure at a distal end of the flexure, a sensing element on the flexure for sensing deflection of the cantilever, and a device for inducing an oscillating deflection of the cantilever relative to the base.

20 Claims, 7 Drawing Sheets

(56) References Cited

U.S. PATENT DOCUMENTS

| | | | | |
|---|---|---|---|---|
| 2011/0159627 A1* | 6/2011 | Mantravadi | ......... | G01P 15/0802 |
| | | | | 438/52 |
| 2011/0313340 A1* | 12/2011 | Judy | ................. | A61M 25/007 |
| | | | | 604/8 |
| 2012/0242189 A1* | 9/2012 | Sulzbach | .............. | B81B 7/0006 |
| | | | | 310/300 |
| 2016/0067464 A1* | 3/2016 | Kim | .................... | A61B 5/0538 |
| | | | | 604/9 |
| 2020/0046951 A1* | 2/2020 | Hoshino | .............. | A61B 5/0059 |

OTHER PUBLICATIONS

Lee, Hyowon et al., "Mechanical Evaluation of Unobstructing Magnetic Microactuators for Implantable Ventricular Catheters," Journal Of Microelectromechanical Systems, vol. 23, No. 4, (2014), pp. 795-802.

Park, Hyunsu et al., "Low-Cost Rapid Prototyping of Liquid Crystal Polymer Based Magnetic Microactuators for Glaucoma Drainage Devices," IEEE (2016) pp. 4212-4215.

Yang, Qi et al., "Anti-Biofouling Implantable Catheter Using Thin-Film Magnetic Microactuators," Sensors & Actuators: B. Chemical 273 (2018) pp. 1694-1704.

Yang, Qi et al., "Piezoresistor-Embedded Multifunctional Magnetic Microactuators for Implantable Self-Clearing Catheter," IEEE Sensors Journal, vol. 19, No. 4, (2019) pp. 1373-1378.

* cited by examiner

MICROACTUATOR SYSTEMS, DRAINAGE DEVICES EQUIPPED THEREWITH, AND METHODS OF USE

CROSS-REFERENCE TO RELATED APPLICATIONS

This application claims the benefit of U.S. Provisional Application No. 62/769,783 filed Nov. 20, 2018, the contents of which are incorporated herein by reference.

STATEMENT REGARDING FEDERALLY SPONSORED RESEARCH

This invention was made with government support under Grant Nos. TR001108 and NS095287, each awarded by the National Institutes of Health. The government has certain rights in the invention.

BACKGROUND OF THE INVENTION

The present invention generally relates to the fields of drainage devices and microactuators. The invention particularly relates to drainage devices equipped with microactuators to provide a self-clearing capability for reducing obstructions and/or a self-monitoring capability to confirm their overall operating condition, and to procedures for implanting and using such devices.

Indwelling catheters are widely used for the treatment and management of various chronic cardiovascular, intravascular, neurological, and urological disorders. The useful lives of indwelling catheters are often limited due to biofouling, resulting in the obstruction of flow through the catheter. For example, chronically implantable shunt systems used for treatment of hydrocephalus have been reported to have a thirty-day shunt failure rate of up to 23 to 26%. U.S. Patent Application Publication No. 2019/0307608, whose contents are incorporated herein by reference, describes self-clearing catheters that utilize thin-film polymer-based magnetic microactuators to combat biofouling-related failures in chronically implanted catheters. The microactuators are deflected out-of-plane by the application of a magnetic field. By applying a time-varying magnetic field, the microactuators can be actuated in a dynamic manner (for example, oscillated or vibrated) such that obstructions, including those caused by biofouling, may be prevented or broken apart and removed without surgical intervention.

Though in vivo evaluations conducted with self-clearing catheters has shown the devices to be efficacious, further operational capabilities would be desirable, including the ability to monitor the mechanical responses of the microactuators as an indication of the orientation of the catheter and verification that the microactuators are operating as intended and confirm the overall operating condition of the catheter.

BRIEF DESCRIPTION OF THE INVENTION

The present invention provides drainage devices and provides microactuator systems adapted to be incorporated into drainage devices to provide a self-clearing capability for reducing obstructions in the drainage devices and/or a self-monitoring capability to confirm the overall operating condition of the drainage devices and their microactuators. The microactuator systems are particularly well suited for, but not limited to, use in indwelling catheters adapted for managing or treating chronic medical conditions, including but not limited to hydrocephalus.

According to one aspect of the invention, a microactuator system is provided that includes a microactuator having a base, a cantilever comprising a flexure extending from the base and a plate structure at a distal end of the flexure, a sensing element on the flexure for sensing deflection of the cantilever, and means for inducing an oscillating deflection of the cantilever relative to the base.

According to another aspect of the invention, methods are provided for operating the microactuator system, as nonlimiting examples, to determine misalignment of the microactuator to the inducing means to determine an orientation of a drainage device to which the microactuator is mounted, to determine a flow rate of a fluid flowing through a drain passage of a drainage device to which the microactuator is mounted, and/or to detect an obstruction within an opening of a drainage device to which the microactuator is mounted and preferably then oscillating the cantilever relative to the base with the inducing means to remove the obstruction from the opening.

Another aspect of the invention is a medical drainage device having a drainage passage, an opening in a wall of the drainage device and fluidically connected to the drain passage, and at least one microactuator disposed in the opening. The microactuator has a base, a cantilever comprising a flexure extending from the base and a plate structure at a distal end of the flexure, and a sensing element on the flexure for sensing deflection of the cantilever. Means is provided for inducing an oscillating deflection of the cantilever relative to the base.

Technical aspects of microactuator systems and drainage devices as described above preferably include the ability to provide a self-clearing capability to address reliability issues of drainage devices relating to biofouling, and further operational capabilities including the ability to monitor the microactuators, as nonlimiting examples, to indicate the orientation of a drainage devices, verify that the microactuator is operating within the drainage device as intended, and/or confirm the overall operating condition of the drainage device.

Other aspects and advantages of this invention will be appreciated from the following detailed description.

BRIEF DESCRIPTION OF THE DRAWINGS

FIG. 6A plots continuous measurements over time while the microactuator was subjected to various flow rates. FIG. 6B plots the change in resistance of the sensing element as a function of flow rate. The predicted values were calculated using a gauge factor (G)=1.1 and a drag coefficient $C_d$=2 (n=3). Flow velocity (v) was calculated from the flow rate (2-15 ml/min) through the catheter (inner diameter (ID)=0.9144 mm). The area (A) of the plate structure was calculated as a circle with a diameter of 850 µm. A water density (p)=1000 Kg/m$^3$ was used.

DETAILED DESCRIPTION OF THE INVENTION

Figure 1A:
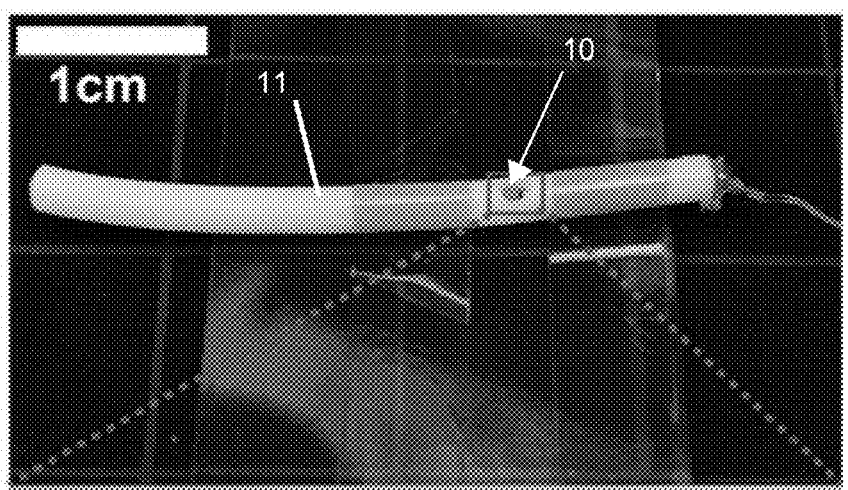
FIG. 1A is an image of a catheter having a magnetically-deflected microactuator mounted thereto to provide self-clearing and self-monitoring capabilities in accordance with a nonlimiting embodiment of the invention.

The following describes microactuator systems and drainage devices that incorporate one or more microactuator systems to enable a self-clearing capability for reducing obstructions in drain passages of the devices, and a monitoring capability for monitoring operational aspects of the devices, as nonlimiting examples, to indicate the orientation of a drainage device, verify that a microactuator is operating within the drainage device as intended, and/or confirm the overall operating condition of the drainage device. Particular but nonlimiting embodiments of drainage devices include ventricular catheters formed of a pliable material (e.g., silicone) and configured to treat hydrocephalus by draining cerebrospinal fluid (CSF) from the brain cavity. One or more microactuators incorporated into a drainage catheter are capable of mechanically inhibiting the formation of obstructions and removing obstructions, for example, as a result of biofouling within a drain passage (lumen) of the catheter, by operating the microactuator(s) to generate shear stresses in the cerebrospinal fluid being drained through the catheter. Though the following discussion will describe microactuators formed of a flexible polymer material and placed within flexible catheters, it should be understood that the invention is not restricted to placement within catheters, and the microactuators could be formed of various materials and placed in flow passages of drainage devices other than catheters.

The monitoring capability of a drainage device that incorporates a remotely-deflectable microactuator includes the ability to measure the amplitude of the deflection of its microactuator to determine the efficacy of the microactuator in situ. According to one aspect of the invention, such a capability can be implemented by integrating a piezoresistive strain sensing element (also simply referred to herein as a piezoresistor) on the microactuator to directly monitor the movement (deflection) of the microactuator. Such a sensing element can be fabricated on a magnetically-deflected microactuator of the type reported in U.S. Patent Application Publication No. 2019/0307608 without significant modification to the process described therein for producing a microactuator.

As known in the art, the piezoresistive effect refers to the change in a material's resistivity due to an applied mechanical strain. For microscale strain sensing, semiconductor materials are typically chosen for their high gauge factors (G), which relates the change in resistance to a baseline resistance and applied strain. For example, single crystal silicon is known to have a gauge factor of greater than 150 and doped diamond films are known to have a gauge factor of greater than 2000. However, semiconductor-based piezoresistors typically require high temperature processes (about 400° C.) for deposition and annealing, which is not compatible with a microactuator fabricated from a flexible polymer material. Although metallic piezoresistors have lower gauge factors, for example, about 1, they can provide adequate sensitivity to generate a detectable signal when sufficiently strained, as is the case with deflections of microactuators suitable for placement in ventricular catheters. Moreover, noble metal piezoresistors are particularly suitable for use in an implantable microdevice due to their biocompatibility and linearity.

The microactuators can be fabricated from various materials, as nonlimiting examples, biocompatible polymers including liquid crystal polymer (LCP) films, poly(vinylidene fluoride) (PVDF), polyimides, parylene, etc., and using various processes, for example, by maskless photolithography, microfabrication techniques of the types used to produce microelectromechanical systems (MEMS), etc. During investigations leading to the present invention, gold (Au) piezoresistive strain sensing elements integrated onto magnetically-deflected thin-film microactuators were demonstrated with sensitivities (0.035%/Deg) and linear ranges (±30°). As discussed below, such microactuators provided additional capabilities including detection of device alignment, flow rate measurement, and obstruction detection in addition to a self-clearing previously described for microactuators disclosed in U.S. Patent Application Publication No. 2019/0307608. The added functionalities enabled by the piezoresistive strain sensing elements promote the ultimate goal of creating a chronically implantable smart catheter that can self-diagnose its status and clear any obstructions without additional surgery.

Figure 1B:
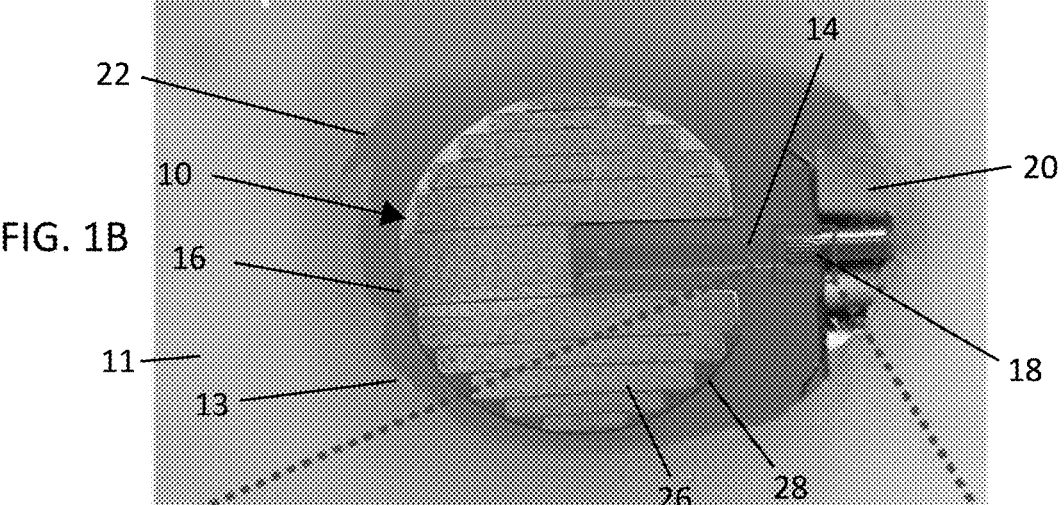
FIG. 1B is a magnified image of the microactuator of FIG. 1A and shows the microactuator as comprising a cantilever that extends into a pore of the catheter.
Figure 1C:
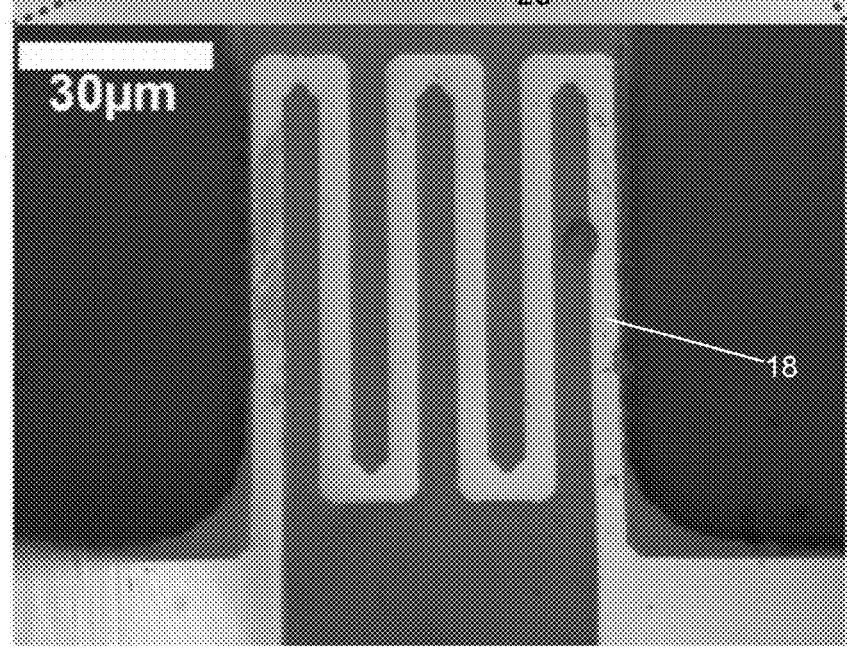
FIG. 1C is a magnified image of a piezoresistive strain sensing element of the microactuator of FIGS. 1A and 1B.
Figure 2:
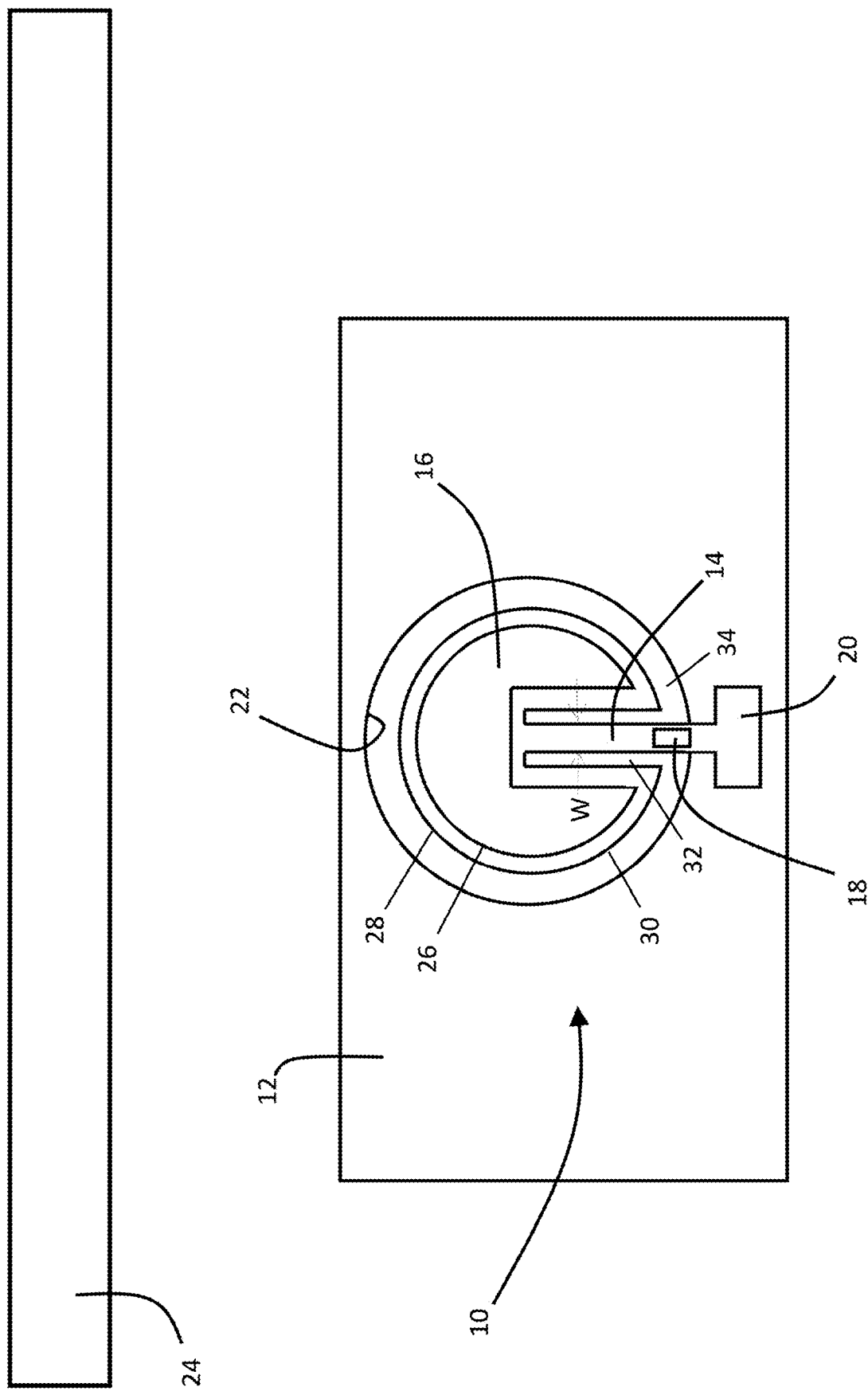
FIG. 2 schematically represents of a microactuator system that includes a magnetically-deflected microactuator of a type shown in FIGS. 1A, 1B, and 1C.

The general structure of the magnetically-deflected thin-film microactuators fabricated for the investigations was similar to those described in Yang et al., "Anti-biofouling implantable catheter using thin-film magnetic microactuators," Sensors and Actuators, B: Chemical, vol. 273, no. June, pp. 1694-1704, 2018 (incorporated herein by reference), and U.S. Patent Application Publication No. 2019/0307608. FIGS. 1A, 1B, and 1C are representative of, respectively, experimental catheters, microactuators, and piezoresistive strain sensing elements evaluated during the investigations. The microactuator 10 shown in FIGS. 1A and 1B is disposed at an opening (pore) 13 in a wall of a catheter 11, and is generally configured as a cantilever that partially spans the pore. The cantilever seen in FIGS. 1A and 1B has a rectangular-shaped polyimide flexure 14 extending from an anchor or base 20, and a plate structure 16 at a distal end of the flexure. The plate structure 16 comprises a nickel ferromagnetic element 26 on a nearly circular polyimide plate 28, and as a result of being formed of a magnetic material enables the flexure 14 to pivot (flex) in response to an applied magnetic field. As seen in FIG. 1B and schematically represented in FIG. 2, the microactuator 10 is fabricated on a substrate 12 to include a cantilever that partially spans an opening 22. The cantilever comprises a rectangular-shaped flexure 14, a plate structure 16 at a distal end of the flexure 14, and a piezoresistive strain sensing element 18 adjacent a base 20 of the flexure 14 where maximum strain occurs corresponding to greater changes in resistance of the sensing element 18. As shown in FIG. 2, the plate structure 16 has a perimeter 30 with a slot 32 therein extending radially from the perimeter 30 to a central area of the plate structure 16. The flexure 14 is partially disposed within the slot 32 of the plate structure 16. The flexure 14 has a width W that is less than the slot 32. The flexure 14 has a portion that is outside of the slot 32 and spans a gap 34 between the base 20 and the perimeter 30 of the plate structure 16. The distal end of the flexure 14 adjoins the plate structure 16 near the center of the plate structure 16. The piezoresistive strain sensing element 18 is disposed on the portion of the flexure 14 between the base 20 and the perimeter 30 of the plate structure 14. FIG. 2 further schematically depicts a magnetic field generating device 24, for example, an electromagnet coil, capable of generating a time-varying magnetic field for inducing an oscillating deflection of the cantilever relative to the base 20 by magnetically coupling with the magnetic material of the plate structure 16.

FIG. 1C is an image of the piezoresistive strain sensing element 18 of FIGS. 1A and 1B. The shape of the sensing element 18 can be seen in FIG. 1C to follow a simple serpentine pattern to maximize the net resistance given the confined space on the flexure. The sensing element 18 has three windings evenly distributed over the width W of the flexure. The entire area of the sensing element 18 including contact pads had a total of 109 effective squares in which 94% was on the region that experiences the most stress during the deflection of the cantilever. The base 20 can be of any suitable construction capable of supporting the cantilever and providing a substrate over which current can be transmitted to and from the piezoresistive strain sensing element 18.

The following describes fabrication steps that were performed to produce the experimental thin-film microactuator used in the investigations, including the microactuator shown in FIGS. 1A-1C. On a 100-mm single-side polished silicon wafer, a 500 nm sacrificial release layer of silicon dioxide ($SiO_2$) was deposited using PECVD. Next, a polyimide layer (PI2525, HD Microsystem, Parlin, N.J.) was spin coated at 1600 rpm and cured in a nitrogen oven. Prior to coating, an adhesion promoter (VM-652, HD Microsystem, Parlin, N.J.) was applied on the release layer to improve adhesion. The thickness of the polyimide was verified to be 10.7 μm using an Alpha-Step IQ surface profiler (KLA-Tencor, Milpitas, Calif.). Next, a piezoresistor (20 nm Cr and 50 nm Au) was deposited on the polyimide layer using an e-beam evaporator (Airco) and patterned using lift-off Following deposition of the piezoresistor, a second layer of polyimide was spin-coated at 8000 rpm to achieve a 1.2 μm thickness. Chromium and gold adhesion and conduction layers were then evaporated on the wafer globally in preparation for nickel (Ni) electroplating an 8 μm-thick Ni ferromagnetic element defined by a plating mold (PR) (AZ9260, MicroChemicals GmbH, Ulm, Germany). Afterwards, the outline of the microactuator, including its plate structure, flexure, and base, were dry-etched using oxygen ($O_2$) plasma (Advanced Oxide Etcher, STS, Newport, UK). The polyimide layers were etched until the $SiO_2$ release layer was exposed. The experimental microactuators were released in a 6:1 buffered oxide etchant that removed the release layer. After the microactuators were detached and collected, the contact pads of the piezoresistors were exposed using an $O_2$ plasma.

The integration of a thin-film microactuator into an implantable catheter requires alignment between the cantilever of the microactuator and the pore of the catheter. Once integrated, the microactuator should be immobilized to withstand a fluid continuously flowing through the lumen of the catheter. Furthermore, electrical connections between the piezoresistor and experimental test equipment were established. To satisfy these requirements, a "needle and thread" integration approach was developed. Two magnet wires were aligned and attached to the contact pads of the piezoresistor. Electrically conductive joints between wires and pads were formed by applying a liquid silver paste (CI-1001, Engineered Conductive Materials, Inc, Delaware, Ohio) and curing on a hotplate at 85° C. for 10 minutes. The wires and microactuator were then transferred and bonded to a polyimide tape for increased structural integrity. Afterwards, the entire microactuator was coated with Parylene C (PDS2010, Specialty Coating System, Indianapolis, Ind.) to improve electrical insulation and biocompatibility. Next, the microactuator was cut to fit inside the lumens of catheters used during the investigations. Using a commercial implantable catheter (Central Venous Catheter Set, Cook Inc.

Bloomington, Ind.), a 1.2-mm-diameter pore was manually punched. The free ends of the two wires were inserted through the pore and pulled out through an open end of the catheter. The microactuator was then drawn through the pore opening to complete the assembly. Once the thin-film microactuator entered the lumen of the catheter, it curled to conform to the inner wall surface of the catheter. Finally, the open end of the catheter with wires was sealed with silicone adhesive. To test the robustness of the integration, deionized water (DI) was manually injected through the remaining catheter opening using a 10 ml syringe. The actuator was able to withstand five consecutive bursts of flow (>5 ml/s) without being dislodged or shifting in position. FIG. 1A is representative of a fully assembled catheter with a piezoresistor-embedded microactuator as described above.

Figure 3:
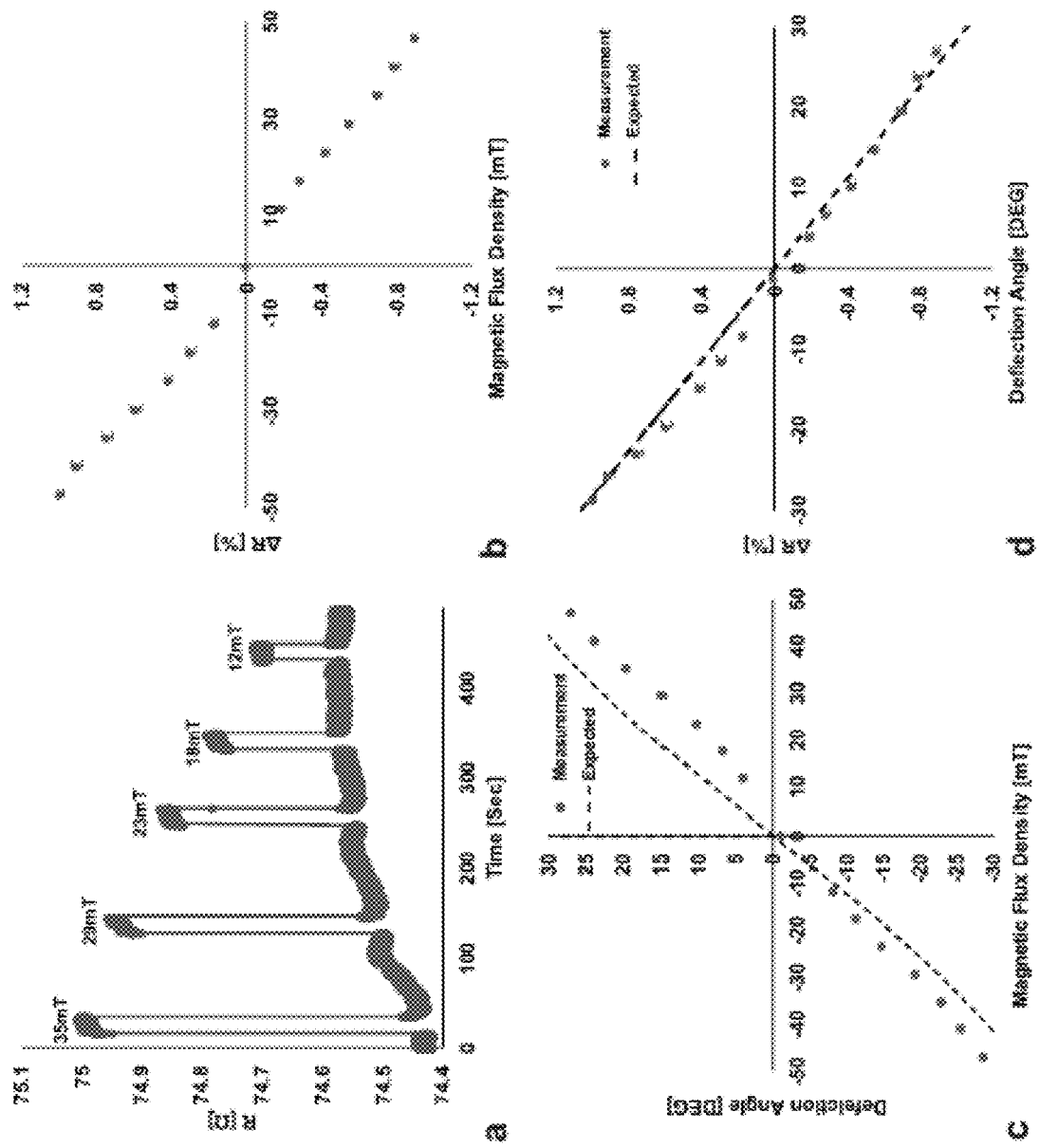
FIG. 3 contains graphs (a) through (d) plotting static characteristics of an experimental piezoresistive strain sensing element integrated onto a magnetically-deflected microactuator of a catheter as represented in FIGS. 1A-1C and 2. The microactuator was fabricated to have a length (L)=655 µm, a width (w)=76 µm, and a thickness (t)=12 µm. Graph (a) plots resistances measured for the microactuator when deflected while subjected to various pulsed magnetic flux densities. Graph (b) plots the percentage of resistance change of the microactuator as a function of actuation strength and actuation direction. A positive change indicates a downward deflection and a negative change indicates an upward deflection (n=3). Graph (c) plots the deflection angle of the microactuator as a function of magnetic flux density (n=3). The theoretical line is calculated using a torque balance equation. Graph (d) plots the percentage of resistance change as a function of deflection angle (n=3). The theoretic line indicates a predicted value of resistance change of G=1.1 for the experimental piezoresistive strain sensing element.

A custom-made electromagnet coil and test fixture were used to assess the performance of piezoresistive strain sensing elements integrated into microactuators placed in catheters as described above. A fundamental function of the sensing element is to indicate a static deflection angle of the microactuator's cantilever as a function of the percentage resistance change of the sensing element. The resistance change of a sensing element integrated onto a microactuator as described above was measured through the wired connection using a custom LabVIEW program (2013, National Instruments, Austin, Tex.) in a four-wire resistance measurement mode. A static deflection response was measured by actuating the device in short magnetic pulses at different magnetic flux densities (10-50 mT) produced by the electromagnet coil in a direction perpendicular to the catheter pore. Static deflection results plotted in FIG. 3 showed that the sensing elements had adequate sensitivity (0.035%/Deg) over a range of −30° to +30°. The predicted percentage change in resistance (R) was calculated by equating the cantilever deflection angle φ to maximum stress $\sigma_{max}$ produced by a point force (F) applied at the distal tip of the microactuator cantilever:

$$\phi = \frac{FL^2}{2EI}; \sigma_{max} = \frac{FLt}{2I}; \quad (1)$$

$$\frac{\Delta R}{R} = G\frac{\sigma_{max}}{E} = \frac{Gt\phi}{L} \quad (2)$$

where L is the cantilever length, t is the cantilever thickness, E is the cantilever elastic modulus (=2.45 GPa for polyimide), and I is the cantilever moment of inertia (=wt³/12 for a rectangular beam). Experimental results portrayed in FIG. 4 indicated that the Au piezoresistor of the sensing element had a gauge factor (G) of 1.1, which corresponded well with values from the literature.

Figure 4:
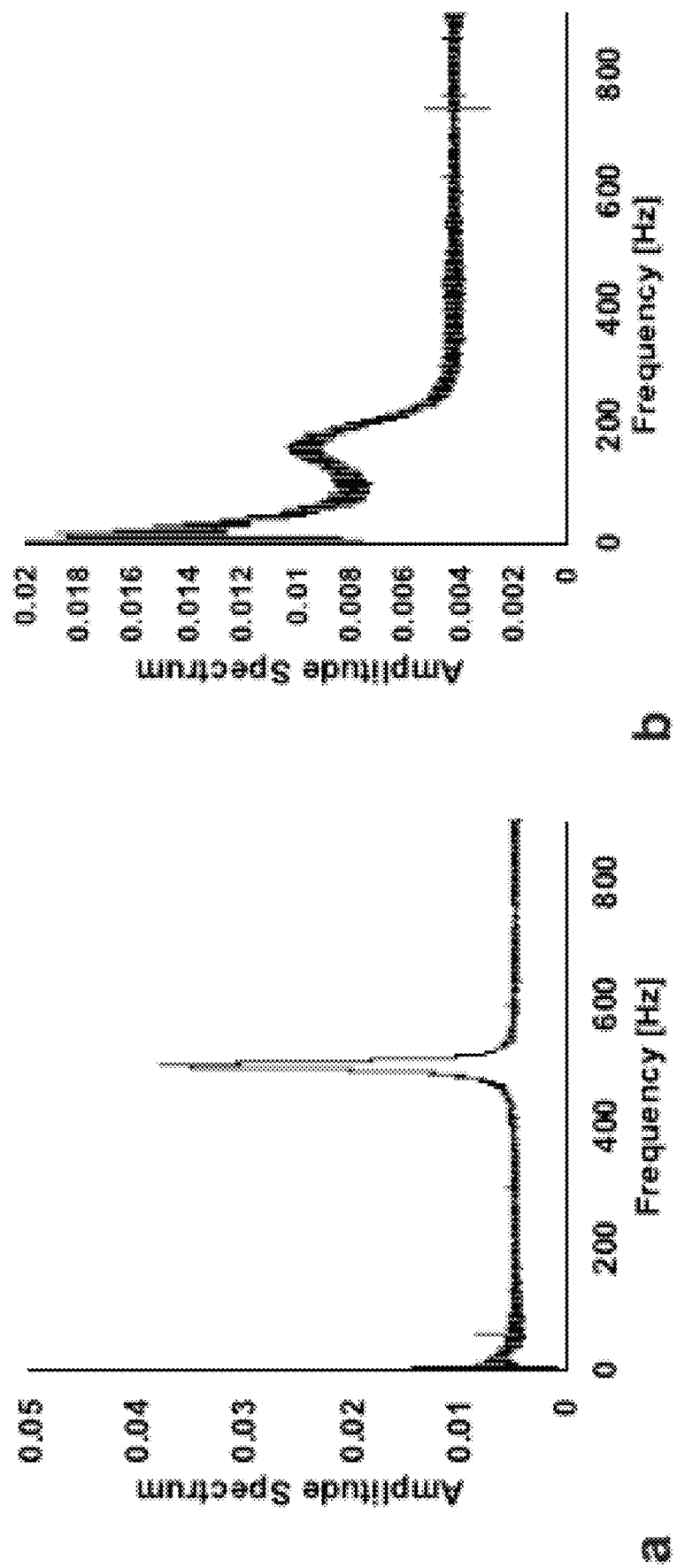
FIG. 4 contains graphs (a) and (b) plotting dynamic characteristics of the experimental piezoresistive strain sensing element whose static characteristics are plotted in FIG. 3. Graph (a) and (b) plot the frequency responses in air and DI water, respectively.

The dynamic response of a microactuator as described above was characterized using its integrated sensing element. A sinusoidal magnetic field (<10 mT) was swept from 5 Hz to 1 kHz in 20 seconds using the aforementioned electromagnet coil. The resistance was sampled at 6.48 kHz and the amplitude spectrum representing the relative deflection was converted into the frequency response using a Fourier transform. FIG. 4 shows the dynamic responses of the microactuator's cantilever in air and in deionized water. The results indicated that the sensing element was able to detect critical dynamic characteristic of the magnetically-deflected microactuator (i.e, resonant frequencies and quality factors).

The ability to minimize the misalignment between the direction of an applied magnetic field relative to the position of a microactuator placed in an implanted catheter is critical to maximizing the deflection of the microactuator. However, it is difficult to ascertain whether a microactuator is fully deflecting once the catheter has been implanted. Even with live fluoroscopic imaging, a microscale device is too small to resolve visually. A sensing element integrated onto a microactuator as described above is able to provide a method to optimize the alignment of the microactuator with an external magnetic field and to determine whether the microactuator's cantilever is actually deflecting.

The relationship between the misalignment angle θ and cantilever deflection angle φ can be described by balancing the mechanical torque ($\tau_{mech}$) and the magnetic torque ($\tau_{mag}$):

$$\tau_{mech} - \tau_{mag} = 0 \quad (3)$$

$$k_\phi - v_m MH \sin\left(\frac{\pi}{2} - \theta - \phi\right) = 0 \quad (4)$$

where $k_\phi$ is the rotational stiffness (=EI/L), $v_m$ is the magnet volume, M is the magnetization (=0.6T for nickel), and H is the applied magnetic field strength. For a given magnetic field strength H, the cantilever deflection angle φ can be solved as a function of the misalignment angle θ. The deflection induced in the cantilever by a magnetic field decreases with greater misalignment of the microactuator to the magnetic field.

Figure 5:
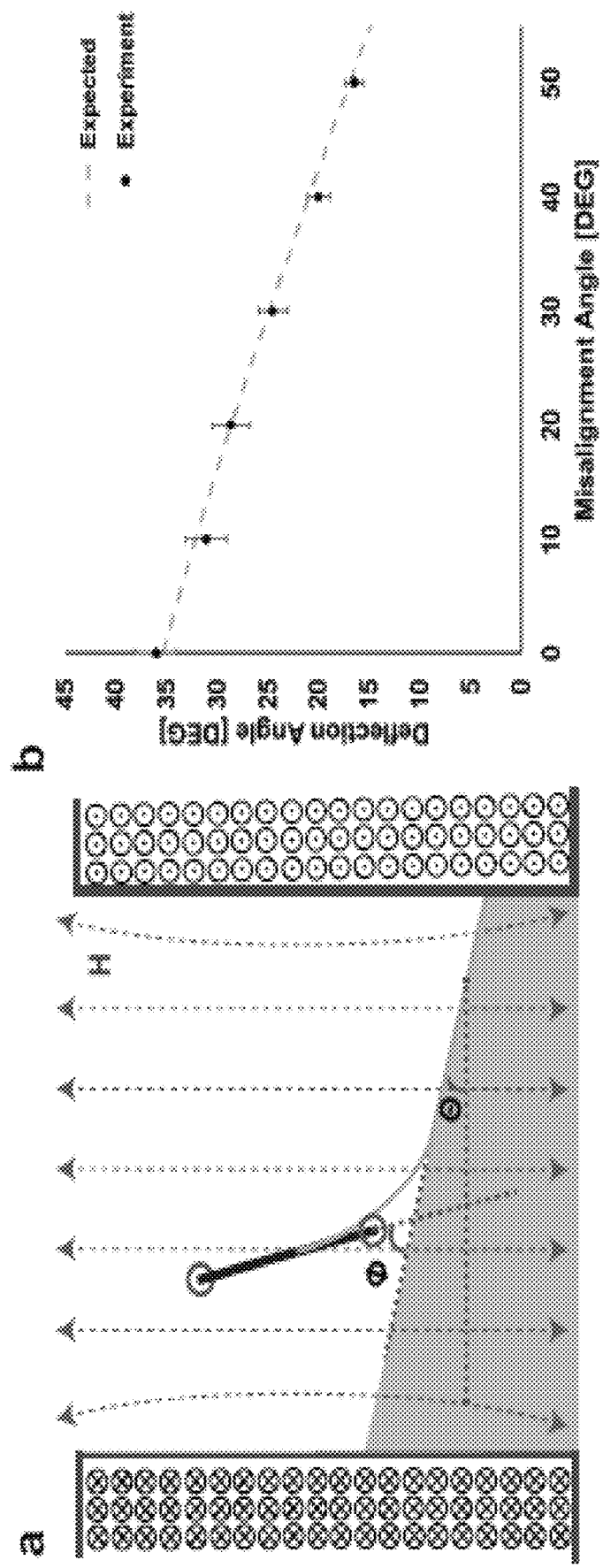
FIG. 5 contains graphs (a) and (b) demonstrating the capability of an experimental piezoresistive strain sensing element to indicate misalignment of a catheter equipped with a magnetically-deflected microactuator onto which a sensing element was integrated as represented in FIGS. 1A-1C and 2. The capability results from the deflection angle ($\Phi$) of the microactuator being influenced if the catheter orientation is not perpendicular (a misalignment angle ($\Theta$) other than zero) to the applied magnetic field. Graph (a) plots the deflection angle as a function of misalignment. For a given magnetic field strength, the deflection angle decreases as a function of the misalignment angle $\theta$. This sensing capability can be used to ensure that the magnetic field is properly oriented to actuate (deflect) the microactuator (n=3). The theoretical line is calculated for the microactuator having a magnet volume ($v_m$)=0.003 mm$^3$, a length (L)=405 µm, a width (w)=7 47.5 µm, and a thickness (t)=12 µm.

Experimentally, the relation between the misalignment of a microactuator as described and the deflection of the microactuator's cantilever was measured using its integrated sensing element. At the center of the electromagnet coil, a catheter having an integrated microactuator as described above was taped at the bottom of a beaker supported by a custom 3D printed test fixture that can tilt, as schematically represented in image (a) of FIG. 5. The text fixture was designed to be fixed at various misalignment angles (0-50° C.) with respect to horizontal. The beaker was filled with DI water to mimic a bodily fluid. For each alignment angle, a magnetic field strength of 20 kA/m was pulsed for 3 seconds. The change in resistance was recorded using a custom LabVIEW DAQ system. Using the previously characterized sensing element calibration, the net deflections of the microactuator's cantilever were estimated (image (b) of FIG. 5). With this alignment information, the orientation of the electromagnetic coil can be adjusted to produce a maximum deflection. In practice, clinicians may be able to utilize this information during the implantation of a catheter to optimize the placement of its microactuator and the electromagnet employed to deflect the microactuator's cantilever.

Microactuator cantilevers as described herein can be passively deflected by a fluid flowing through a catheter as well as actively deflected with an applied magnetic field. As such, the deflection of the microactuator can be characterized using its integrated sensing element to indicate the flow rate of a fluid flowing through a catheter in which the microactuator has been integrated. For example, as cerebrospinal fluid drains through a pore of a ventricular catheter, the fluid applies a drag force to a microactuator cantilever placed at the pore, causing the cantilever to bend and inducing a resistance change in its sensing element that can be estimated by modeling the fluid drag $F=\frac{1}{2}\rho v^2 C_d A$ on a perpendicular thin plate, where ρ is the fluid density, v is the fluid velocity, $C_d$ is the drag coefficient of the plate structure, and A is the surface area of the plate structure. The stress at the base of the cantilever can be derived by assuming a point force (F) concentrated at the distal tip of the cantilever. The resistance change can then be described as $$\Delta R = \frac{\rho v^2 C_d ARGLt}{4EI} \quad (5)$$

Figures 6A, 6B:
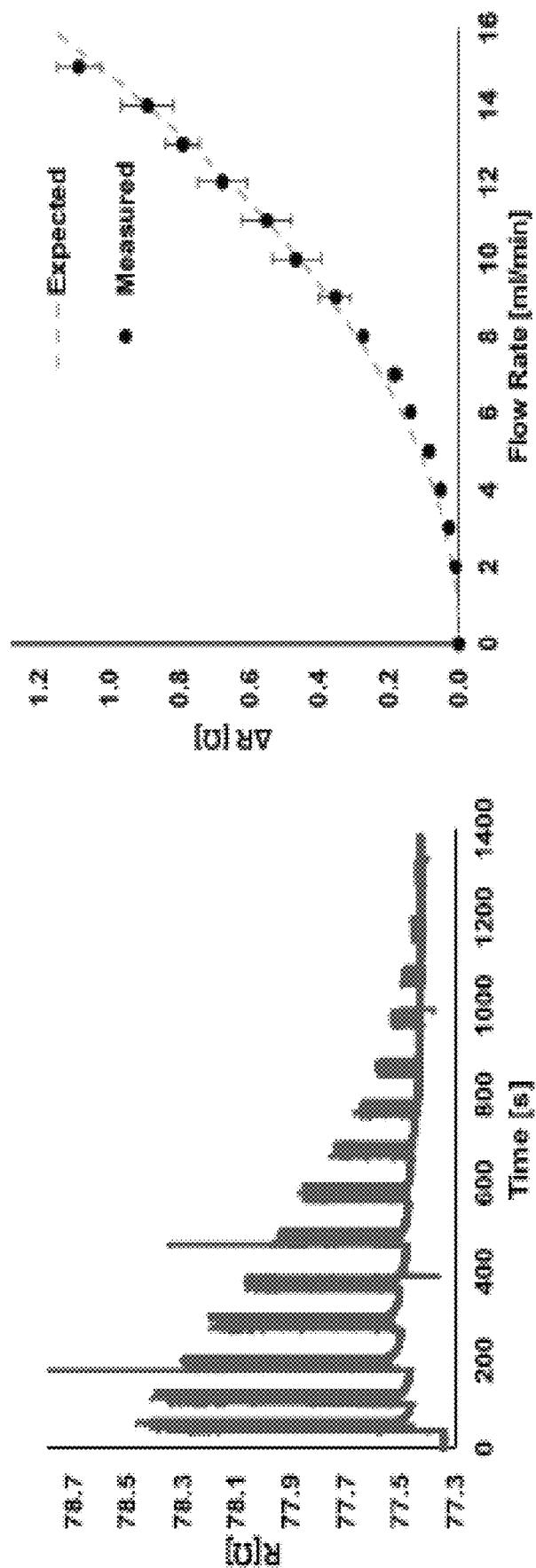
FIGS. 6A and 6B are graphs demonstrating the capability of an experimental piezoresistive strain sensing element to indicate flow rate through a catheter equipped with a magnetically-deflected microactuator onto which a sensing element was integrated as represented in FIGS. 1A-1C and 2. The microactuator had a length (L)=655 µm, width (w)=76 µm, and thickness (t)=12 µm).

Bench-top experiments were performed to characterize the flow rate-resistance relationship as a means for indicating the flow rate of a fluid through a catheter in which a microactuator has been integrated as described above. In an evaporating dish, such a catheter was immobilized and submerged in DI water. DI water was pumped through the open end of the catheter and the volume flow rate was calibrated by measuring the mass of the pumped water. The pump was driven at various flow rates (2-15 ml/min with 1 ml/min decrement) and corresponding resistance changes relative to the baseline values were measured (FIGS. 6A and 6B). The change in resistance matched Eq. 5 well, which suggested a good flow sensing capability for the tested range.

Figure 7:
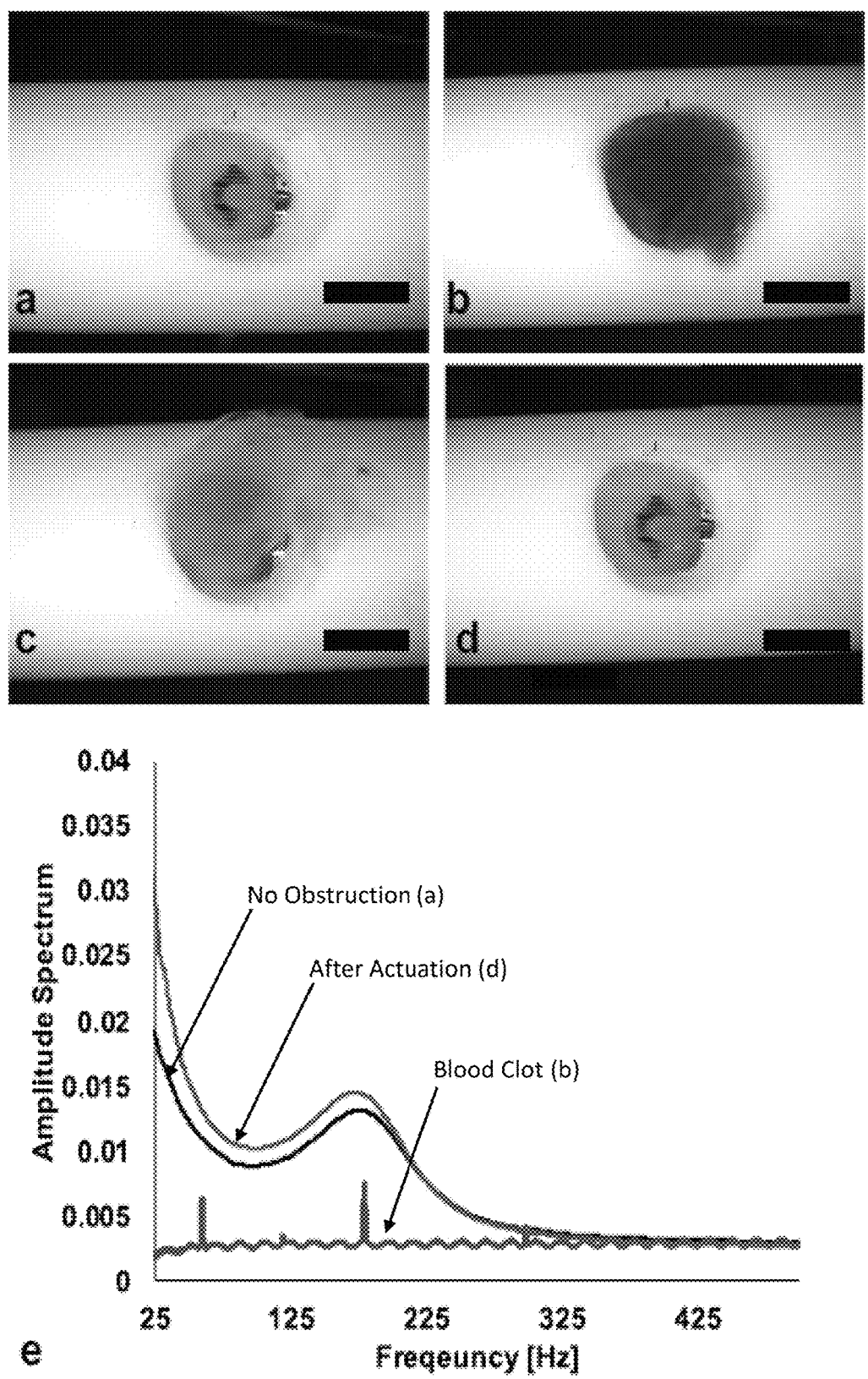
FIG. 7 contains four images (a through d) and a graph (e) demonstrating the capability of an experimental magnetically-deflected microactuator as represented in FIGS. 1A-1C and 2 to detect and clear an obstruction (blood clot occlusion) in an inlet pore of a catheter into which the microactuator is cantilevered. Image (a) shows a portion of the catheter before occlusion, Image (b) shows the catheter with the obstruction occluding the inlet pore, Image (c) shows the catheter during oscillation (vibration) of the microactuator to remove the obstruction, and Image (d) shows the catheter after the obstruction was cleared by vibrating the microactuator. The scale bar in each of Images (a) through (d) is 1 mm. Graph (e) plots the frequency response of the microactuator before and after removal of the obstruction. When the obstruction occluded the inlet pore, the dynamic response of the microactuator was completely attenuated. Following removal of the obstruction, the dynamic response was restored to show characteristic peaks.

A significant clinical challenge for chronic use of an indwelling catheter is to non-invasively determine whether the catheter is failing or its function otherwise impeded due to an obstruction within its lumen. The ability to monitor the dynamic responses of a microactuator as described above makes possible the ability to detect the presence of an obstruction at a pore of the catheter while the catheter remains implanted. To demonstrate, the baseline dynamic responses was measured of an experimental microactuator integrated into a catheter as described above. Images (a) through (d) of FIG. 7 (a) are images of a portion of the catheter that includes its pore and a microactuator placed at the pore as previously described. Image (e) of FIG. 7 is a graph plotting the baseline dynamic response of the microactuator, evidencing the characteristic peaks of the dynamic response. Image (a) of FIG. 7 shows the catheter and its pore free of any occlusion.

A blood clot was made using a blood sample from an euthanized pig by dropping 2 ml of the blood into 0.1 M phosphate buffer solution (PBS, pH 7, Fisher Scientific, Waltham, Mass.). The resulting blood clot mass was then gently squeezed into the pore of the catheter to mimic a robust obstruction (image (b) of FIG. 7). The dynamic response of the device was measured again and is plotted in image (e) of FIG. 7. With the blood clot obstructing the movement of the microactuator, the dynamic response can be seen in image (e) to be significantly suppressed. Next, a low-frequency high-amplitude actuation was magnetically applied (20 Hz at 25 kA/m) to the microactuator for 3 minutes (image (c) of FIG. 7), during which time the blood clot was dislodged and removed (image (d) of FIG. 7). Finally, the dynamic response of the microactuator was captured again to demonstrate the restoration of its characteristic peaks. This investigation evidenced the ability of the microactuator to not only remove an obstruction within a catheter, but also to detect the presence of the obstruction by observing the dynamic response of the microactuator while the catheter remains implanted, and therefore without the need for performing surgery to assess the catheter.

In view of the above, it can be appreciated that the fabricated and tested flexible magnetically-deflected microactuators with integrated piezoresistive strain sensing elements were able to improve the functionality of a chronically implantable catheter. By monitoring the resistance change as a function of microactuator deflection, it can be determined whether a catheter and its pore (or pores) are aligned to provide maximum deflection of the microactuator. The resistance changed linearly over the tested deflection range, and corresponded well with the predicted values. Also demonstrated was the ability to monitor fluid flow with the microactuators, which may be used to monitor the fluid flow rate in situ. The microactuators were also shown to be capable of detecting the presence of an obstruction within a catheter.

On the basis of the above investigations, it was concluded that microactuators as described above and/or shown in the drawings should be capable of being integrated into the lumen of a ventricular catheter to prevent the lumen from becoming obstructed. Both static and dynamic responses suggested good control of the fabrication processes, and the actuation of the microactuators was shown to be capable of removing blood clots and other proteinaceous biofouling within the catheter and on surfaces of the microactuators.

While the invention has been described in terms of particular embodiments and investigations, it should be apparent that alternatives could be adopted by one skilled in the art. For example, the microactuators and their sensing elements could differ in appearance and construction from the embodiments described herein and shown in the drawings, functions of certain components of the microactuators and their sensing elements could be performed by components of different construction but capable of a similar (though not necessarily equivalent) function, and appropriate materials could be substituted for those noted. In addition, the above detailed description is intended to describe the particular embodiments represented in the drawings and certain but not all features and aspects thereof, and to identify certain but not all alternatives to the embodiments and described features and aspects. As a nonlimiting example, the invention encompasses additional or alternative embodiments in which one or more features or aspects of a particular embodiment could be eliminated. Accordingly, it should be understood that the invention is not necessarily limited to any embodiment described herein or illustrated in the drawings, and the phraseology and terminology employed above are for the purpose of describing the illustrated embodiments and investigations and do not necessarily serve as limitations to the scope of the invention. Therefore, the scope of the invention is to be limited only by the following claims.

The invention claimed is:

1. A microactuator system for use with a drainage device, the microactuator system comprising:
   a microactuator comprising a base, a cantilever comprising a flexure extending from the base and a plate structure at a distal end of the flexure, and a strain sensing element on the flexure for sensing deflection of the cantilever;
   means for inducing an oscillating deflection of the cantilever relative to the base, the inducing means comprising a magnetic field generating device that generates an external magnetic field;
   wherein the strain sensing element senses deflection of the cantilever while the external magnetic field acts on the microactuator; and
   wherein the strain sensing element is configured for optimizing alignment of the microactuator with the external magnetic field, whereby sensed strain of the strain sensing element is calibrated relative to the external magnetic field to establish a relationship between a deflection angle of the cantilever and a misalignment angle between the cantilever and the external magnetic field, the relationship being operable to indicate misalignment between the cantilever and the external magnetic field and enable optimizing the alignment of the microactuator with the external magnetic field based on the sensed strain from the strain sensing element.

2. The microactuator system according to claim 1, wherein the external magnetic field is a time varying magnetic field and the plate structure comprises a magnetic material.

3. The microactuator system according to claim 1, wherein the strain sensing element is a piezoresistive strain sensing element arranged in a serpentine pattern.

4. The microactuator system according to claim 1, wherein the microactuator is formed of biocompatible materials.

5. The microactuator system according to claim 1, wherein the plate structure is anchored to the base solely by the flexure.

6. The microactuator system according to claim 1, wherein the sensing element is located where the flexure adjoins the base.

7. The microactuator system according to claim 1, wherein the microactuator is mounted to a drainage device and the cantilever is disposed in a pore of the drainage device.

8. The microactuator system of claim 7, wherein the drainage device is a ventricular catheter.

9. A method of operating the microactuator system of claim 1, the method comprising using the sensing element to determine misalignment of the microactuator to the inducing means to determine an orientation of a drainage device to which the microactuator is mounted.

10. A method of operating the microactuator system of claim 1, the method comprising using the sensing element to determine a flow rate of a fluid flowing through a drain passage of a drainage device to which the microactuator is mounted.

11. A method of operating the microactuator of system of claim 1, the method comprising using the sensing element to detect an obstruction within an opening of a drainage device to which the microactuator is mounted.

12. The method of operating the microactuator system of claim 11, the method comprising oscillating the cantilever relative to the base with the inducing means to remove the obstruction from the opening of the drainage device.

13. A medical drainage device comprising:
a drainage passage;
an opening in a wall of the drainage device and fluidically connected to the drain passage;
at least one microactuator disposed in the opening, the microactuator comprising a base, a cantilever comprising a flexure extending from the base and a plate structure at a distal end of the flexure, and a strain sensing element on the flexure for sensing deflection of the cantilever;
means for inducing an oscillating deflection of the cantilever relative to the base, the inducing means comprising a magnetic field generating device that generates an external magnetic field;
wherein the strain sensing element senses deflection of the cantilever while the external magnetic field acts on the microactuator; and
wherein the strain sensing element is configured for optimizing alignment of the microactuator with the external magnetic field, whereby sensed strain of the strain sensing element is calibrated relative to the external magnetic field to establish a relationship between a deflection angle of the cantilever and a misalignment angle between the cantilever and the external magnetic field, the relationship being operable to indicate misalignment between the cantilever and the external magnetic field and enable optimizing the alignment of the microactuator with the external magnetic field based on the sensed strain from the strain sensing element.

14. The medical drainage device according to claim 13, wherein the external magnetic field is a time varying magnetic field and the plate structure comprises a magnetic material.

15. The medical drainage device according to claim 13, wherein the sensing element is a piezoresistive strain sensing element.

16. The medical drainage device according to claim 13, wherein the microactuator is formed of biocompatible materials.

17. The medical drainage device according to claim 13, wherein the plate structure is anchored to the base solely by the flexure.

18. The medical drainage device microactuator system according to claim 3, wherein:
the plate structure has a perimeter with a slot therein;
the flexure is partially disposed within the slot of the plate structure, has a width that is less than the slot, and has a portion that is outside of the slot and spans a gap between the base and the perimeter of the plate structure;
the distal end of the flexure adjoins the plate structure at a center of the plate structure; and
the piezoresistive strain sensing element is disposed on the portion of the flexure between the base and the perimeter of the plate structure.

19. The medical drainage device according to claim 13, wherein the sensing element is located where the flexure adjoins the base.

20. The medical drainage device according to claim 13, wherein the drainage device is a ventricular catheter.

* * * * *